(12) United States Patent
Schaeffer-Korbylo et al.

(10) Patent No.: US 10,563,243 B2
(45) Date of Patent: Feb. 18, 2020

(54) BIOAVAILABILITY OF METAL IONS

(71) Applicant: Colgate-Palmolive Company, New York, NY (US)

(72) Inventors: Lyndsay Schaeffer-Korbylo, Flemington, NJ (US); Betty Won, Princeton Junction, NJ (US); Venda Porter Maloney, Piscataway, NJ (US); Gregory Szewczyk, Flemington, NJ (US)

(73) Assignee: Colgate-Palmolive Company, New York, NY (US)

( * ) Notice: Subject to any disclaimer, the term of this patent is extended or adjusted under 35 U.S.C. 154(b) by 113 days.

(21) Appl. No.: 15/509,901

(22) PCT Filed: Sep. 24, 2014

(86) PCT No.: PCT/US2014/057249
§ 371 (c)(1),
(2) Date: Mar. 9, 2017

(87) PCT Pub. No.: WO2016/048304
PCT Pub. Date: Mar. 31, 2016

(65) Prior Publication Data
US 2017/0247740 A1 Aug. 31, 2017

(51) Int. Cl.
*C12Q 1/18* (2006.01)

(52) U.S. Cl.
CPC .......... *C12Q 1/18* (2013.01); *C12Q 2304/22* (2013.01); *C12Q 2304/24* (2013.01)

(58) Field of Classification Search
CPC .... A61K 31/045; A61K 31/047; A61K 31/14; A61K 31/198; A61K 31/341; A61K 31/4425; A61K 45/06; A61K 9/1075; A61K 2300/00; A61K 47/34; A61K 47/10; A61K 47/26; A61K 9/06; A61K 47/64; A61K 38/08; A61K 38/10; A61K 38/16; A61K 41/0009; A61K 41/0057; A61K 41/0071; A61K 47/6911; A61K 8/64; A61K 9/0019; A61K 9/0063; A61K 31/155; A61K 36/30; A61K 36/328; A61K 8/27; A61K 8/21; A61K 8/24; A61K 8/25; A61K 8/463; A61K 2800/70; A61K 33/00; A61K 8/44; A61K 8/442; A61K 47/18; A61K 47/186; A61K 47/38; A61K 47/6425; A61K 47/6839; A61K 47/6843; A61K 47/6849; A61K 8/36; A61K 9/0014; A61K 9/006; A61K 2800/20; A61K 2800/58; A61K 2800/92; A61K 31/216; A61K 31/225; A61K 31/352; A61K 33/30; A61K 36/45; A61K 36/534; A61K 36/54; A61K 8/0216; A61K 8/062; A61K 8/30; A61K 8/33; A61K 8/34; A61K 8/347; A61K 8/362; A61K 8/365; A61K 8/37; A61K 8/416; A61K 8/58; A61K 8/922; A61K 9/08; A61K 9/1658; A61K 8/0245; A61K 8/19; A61K 2800/412; A61K 2800/5922; A61K 2800/594; A61K 2800/624; A61K 8/29; A61K 8/731; A61K 8/361; A61K 2800/43; A61K 2800/621; A61K 2800/651; A61K 8/0241; A61K 8/345; A61K 8/466; A61K 8/8164; A61K 8/8176; A61K 2800/30; A61K 2800/882; A61K 8/22; C12Q 1/18; C12Q 2304/22; C12Q 2304/24; C12Q 1/025; C12Q 1/68; C12Q 1/6813; A23G 3/36; A23G 3/48; A23G 4/06; A23G 4/068; A61Q 11/00; A61Q 17/005; A61Q 11/02; A61Q 5/006; C07K 14/001; C07K 7/06; C07K 7/08; C07K 2319/00; C07K 2319/01; C07K 14/245; C07K 14/395; C07K 14/78; C07K 2319/33; A01N 37/46; A23V 2002/00; A23V 2250/1842; A23V 2250/21; A23V 2250/5026; A23V 2250/5036; A23V 2250/51084; A23V 2250/5114; A23V 2250/6406; G01N 33/569; G01N 21/78; G01N 33/5082; G01N 33/84; Y02A 50/47; Y02A 50/473; C12N 15/62; C12N 9/00;
(Continued)

(56) References Cited

U.S. PATENT DOCUMENTS 7,790,140 B2  9/2010  Bolotin
8,007,846 B2  8/2011  Thompson et al.
(Continued)

FOREIGN PATENT DOCUMENTS

CN  102925401 A  2/2013
EP  1367134     12/2003
(Continued)

OTHER PUBLICATIONS

International Search Report and Written Opinion in International Application No. PCT/US2014/057249, dated Jun. 22, 2015.
Lansdown et al., 2006, "Silver in health care: Antimicrobial effects and safety in use," Current Problems in Dermatology 33:17-34.
Leth et al., 2001, "Engineered bacteria. based biosensors for monitoring bioavailable heavy metals," Electroanalysis 14(1):35-42.
(Continued)

*Primary Examiner* — Deborah K Ware

(57) ABSTRACT

Provided herein is a method for determining the bioavailability of a metal ion in a composition comprising a source of the metal ion, wherein the metal ion has antimicrobial activity, and wherein the method comprises: a) incubating a sample of the composition with bacterial cells, and b) determining the viability of the bacterial cells after incubation. The method is useful for determining the effect of agents on the bioavailability of metal ions in a composition.

21 Claims, No Drawings

(58) Field of Classification Search
CPC .... C12N 9/50; C12N 15/8243; C12N 9/6427; A61L 2300/206; A61L 2300/30; A61L 2300/404; A61L 2430/34; A61L 26/0019; A61L 26/0023; A61L 26/0052; A61L 26/0057; A61L 26/0066; A61L 26/008; A61P 1/02; C12P 13/06; C12P 13/08; C12P 1/00; C12Y 101/05002; A23L 27/79
See application file for complete search history.

(56) References Cited

U.S. PATENT DOCUMENTS

| | | | |
|---|---|---|---|
| 8,067,627 B2 | 11/2011 | Newsome et al. | |
| 8,211,410 B2 | 7/2012 | Baig et al. | |
| 8,216,553 B2 | 7/2012 | Hughes et al. | |
| 8,252,322 B2 | 8/2012 | Trubiano et al. | |
| 8,283,135 B2 | 10/2012 | Doyle et al. | |
| 8,293,216 B2 | 10/2012 | Deckner et al. | |
| 8,303,989 B2 | 11/2012 | Choi et al. | |
| 8,524,269 B2 | 9/2013 | Schramm et al. | |
| 8,962,026 B2 * | 2/2015 | Baker, Jr. | A61K 9/1075 424/400 |
| 9,259,407 B2 * | 2/2016 | Baker, Jr. | A61K 9/1075 |
| 9,625,449 B2 * | 4/2017 | Jaracz | G01N 33/5082 |
| 2002/0193351 A1 | 12/2002 | Taylor | |
| 2006/0286627 A1 * | 12/2006 | Bochner | G01N 33/5023 435/40.5 |
| 2008/0090297 A1 | 4/2008 | Richards | |
| 2009/0275496 A1 | 11/2009 | Baldwin et al. | |
| 2010/0143430 A1 | 6/2010 | King et al. | |
| 2010/0143495 A1 | 6/2010 | Hill et al. | |
| 2011/0189260 A1 | 8/2011 | Herr et al. | |
| 2012/0064017 A1 * | 3/2012 | Porter | A61K 8/58 424/57 |
| 2013/0123355 A1 | 5/2013 | Chopra | |

FOREIGN PATENT DOCUMENTS

| | | |
|---|---|---|
| WO | WO 1993/016382 | 8/1993 |
| WO | WO 2006/012967 | 2/2006 |
| WO | WO 2009/140215 | 11/2009 |
| WO | WO 2010/065090 | 6/2010 |
| WO | WO 2014/059417 | 4/2017 |

OTHER PUBLICATIONS

Said et al., 2014, "An in vitro test of the efficacy of silver-containing wound dressings against *Staphylococcus aureus* and Pseudomonas aeruginosa in simulated wound fluid," International J. of Pharmaceutics 462(1):123-128.

Xiu et al., 2011, Differential effect of common ligands and molecular oxygen on antimicrobial activity of silver nanoparticles versus silver ions, Environmental Science & Technology 45(20):9003-9008.

* cited by examiner

BIOAVAILABILITY OF METAL IONS

CROSS-REFERENCE TO RELATED APPLICATIONS

This application is a national stage entry under 35 U.S.C. § 371 of International Patent Application No. PCT/US2014/057249, filed on Sep. 24, 2014, the contents of which are hereby incorporated by reference in its entirety.

BACKGROUND

Many metal ions (for example, copper, cobalt, silver, manganese, nickel and zinc) are known to have antimicrobial activity. Their modes of action remain unclear but may involve oxidative stress, protein dysfunction of membrane damage in the target cell. Sources of metal ions (for example, metal salts) are often incorporated into oral care formulations to impart antimicrobial properties to the compositions.

Current methods to determine the bioavailability of metal ions in compositions (i.e. the extent to which the metal ions can act at the desired physiological site to bring about the desired clinical or biological effect), rely on measuring the amount of soluble ions in the compositions. Typically in these methods, the compositions are centrifuged to pellet insoluble material, and the amount of a given metal ion in the resulting cleared supernatant is measured to determine the amount of soluble, and thus "bioavailable" metal ions.

However, measuring solubility of metal ions alone may not provide accurate indication of bioavailability. For example, soluble ions may inadvertently be retained in the insoluble fraction following centrifugation and decanting of the supernatant (tzar example, through adsorption onto solids).

It would therefore be desirable to provide an improved method of determining the bioavailability of metal ions which do not rely on solubility alone.

BRIEF SUMMARY

The present inventors have found that measuring the amount of metal ions in a soluble fraction of a composition is generally not a good indicator of the bioavailability of the metal ions. The inventors have developed a more effective method of determining the bioavailability of metal ions in a composition based on the ability of the metal ions to modulate bacterial metabolism and/or growth.

Accordingly, in a first aspect, there is provided a method for determining the bioavailability of a metal ion in a composition comprising a source of the metal ion, wherein the metal ion has antimicrobial activity, and wherein the method comprises:
a) incubating a sample of the composition comprising the source of the metal ion with bacterial cells, and
b) determining the viability of the bacterial cells after incubation.

Optionally, the composition further comprises a chelating agent. Further optionally, the chelating agent is selected from tetrasodium pyrophosphate (TSPP), tetrapotassium pyrophosphate (TKPP), sodium tripolyphosphate (STPP), and ethylenediamine tetra-acetic acid (EDTA). Still further optionally, the composition consists essentially of water, the metal ion, and a chelating agent.

Optionally, the composition is an oral care composition or a skin care composition. Optionally, the oral care composition further comprises one or more agents selected from: surfactants, desensitizing agents, whitening agents, tartar control agents, binders, thickening agents, detergents, adhesion agents, foam modulators, pH modifying agents, mouth feel agents, sweeteners, flavorants, colorants, humectants, fluoride sources and combinations thereof. Optionally, the skin care composition further comprises one or more agents selected from: dyes, fragrances, pH modifying agents, thickeners, viscosity modifiers, buffering agents, antioxidants, chelating agents, opacifiers, and humectants.

Optionally, in step b), the viability of the bacterial cells is determined using a metabolic indicator dye. Preferably, the metabolic indicator dye comprises a redox-sensitive indicator dye. More preferably, the metabolic indicator dye comprises a tetrazolium-based dye. Most preferably, the metabolic indicator dye comprises a dye selected from 3-(4,5-dimethylthiazol-2-yl)-2,5-diphenyltetrazolium bromide (MTT), 2,3-bis-(2-methoxy-4-nitro-5-sulfophenyl)-2H-tetrazolium-5-carboxanilide (XTT), 3-(4,5-dimethylthiazol-2-yl)-5-(3-carboxymethoxyphenyl)-2-(4-sulfophenyl)-2H-tetrazolium) (MTS), and 2-(2-methoxy-4-nitrophenyl)-3-(4-nitrophenyl)-5-(2,4-disulfophenyl)-2H-tetrazolium) (WST).

Optionally, the metabolic indicator dye comprises 7-Hydroxy-3H-phenoxazin-3-one 10-oxide (resazurin).

Preferably, the bacterial cells are selected from *Actinomyces viscosus, Lactobacillus casei, Streptococcus oralis, Fusobacterium nucleatum, Veillnoella parvula, Escherichia coli, Staphylococcus aureus* and *Serratia marcescens*, or a mixture thereof. Optionally, the bacterial cells comprise *Actinomyces viscosus, Lactobacillus casei, Streptococcus oralis, Fusobacterium nucleatum*, and *Veillnoella parvula*. Further optionally, the bacterial cells comprise *Escherichia coli, Staphylococcus aureus* and *Serratia marcescens*.

Optionally, the source of the metal ion is a salt of the metal ion.

Preferably, the metal ion is selected from copper, cobalt, silver, manganese, nickel and zinc. More preferably, the metal ion is zinc. Most preferably, the source of zinc comprises one or more of zinc chloride, zinc citrate and zinc oxide.

Optionally, step b) comprises quantitatively determining the viability of the bacterial cells after incubation by comparison to standard combinations of viable and non-viable bacterial cells.

In a second aspect, there is provided a use of the method as defined herein, to determine the antimicrobial efficacy of a composition comprising a metal ion source. The composition may be as defined herein.

In a third aspect, there is provided a use of the method as defined herein to evaluate the effect of an agent, preferably an oral care agent or a skin care agent, on the bioavailability of a metal ion in a composition comprising a source of the metal ion and the agent. The composition may be as defined herein.

In a fourth aspect, there is provided a method of assessing the effect of an agent on the bioavailability of a metal ion in a composition comprising a source of the metal ion, wherein the metal ion has antimicrobial activity, and the method comprises:
a) incubating a first sample of the composition comprising the source of the metal ion with bacterial cells,
b) determining the viability of the bacterial cells after incubation,
c) incorporating the agent into a second sample of the composition comprising the source of the metal ion,
d) incubating the second sample of the composition comprising the source of the metal ion and the agent with bacterial cells, e) determining the viability of the bacterial cells after incubation, and f) comparing the viabilities determined in steps b) and e).

Optionally, the agent is a chelating agent. Further optionally, the chelating agent is selected from tetrasodium pyrophosphate (TSPP), tetrapotassium pyrophosphate (TKPP), sodium tripolyphosphate (STPP), and ethylenediamine tetra-acetic acid (EDTA). Still further optionally, the composition consists essentially of water, the metal ion, and a chelating agent.

Optionally, the agent is an oral care agent or a skin care agent.

Optionally, the composition is an oral care composition or a skin care composition. Preferably, the oral care composition further comprises one or more agents selected from: surfactants, desensitizing agents, whitening agents, tartar control agents, binders, thickening agents, detergents, adhesion agents, foam modulators, pH modifying agents, mouth feel agents, sweeteners, flavorants, colorants, humectants, fluoride sources and combinations thereof.

Optionally, the composition is a skin care composition. Preferably, the skin care composition further comprises one or more agents selected from: dyes, fragrances, pH modifying agents, thickeners, viscosity modifiers, buffering agents, antioxidants, chelating agents, opacifiers, and humectants.

Optionally, in steps b) and e), the viability of the bacterial cells is determined using a metabolic indicator dye. Preferably, the metabolic indicator dye comprises a redox-sensitive indicator dye. More preferably, the metabolic indicator dye comprises a tetrazolium-based dye. Most preferably, the metabolic indicator dye comprises a dye selected from 3-(4,5-dimethylthiazol-2-yl)-2,5-diphenyltetrazolium bromide (MTT), 2,3-bis-(2-methoxy-4-nitro-5-sulfophenyl)-2H-tetrazolium-5-carboxanilide (XTT), 3-(4,5-dimethylthiazol-2-yl)-5-(3-carboxymethoxyphenyl)-2-(4-sulfophenyl)-2H-tetrazolium) (MTS), and 2-(2-methoxy-4-nitrophenyl)-3-(4-nitrophenyl)-5-(2,4-disulfophenyl)-2H-tetrazolium) (WST).

Optionally, the metabolic indicator dye comprises 7-Hydroxy-3H-phenoxazin-3-one 10-oxide (resazurin).

Preferably, the bacterial cells are selected from *Actinomyces viscosus, Lactobacillus casei, Streptococcus oralis, Fusobacterium nucleatum, Veillnoella parvula, Escherichia coli, Staphylococcus aureus* and *Serratia marcescens*, or a mixture thereof. Optionally, the bacterial cells comprise *Actinomyces viscosus, Lactobacillus casei, Streptococcus oralis, Fusobacterium nucleatum*, and *Veillnoella parvula*. Further optionally, the bacterial cells comprise *Escherichia coli, Staphylococcus aureus* and *Serratia marcescens*.

Optionally, the source of the metal ion is a salt of the metal ion.

Preferably, the metal ion is selected from copper, cobalt, silver, manganese, nickel and zinc. More preferably, the metal ion is zinc. Most preferably, the source of zinc comprises one or more of zinc chloride, zinc citrate and zinc oxide.

Optionally, steps b) and e) comprise quantitatively determining the viability of the bacterial cells after incubation by comparison to standard combinations of viable and non-viable bacterial cells.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

In one arrangement, provided herein is a method for determining the bioavailability of metal ions in a composition comprising a source of the metal ions, wherein the metal ions have antimicrobial activity, and wherein the method comprises:

a) incubating a sample of the composition comprising the metal ion with bacterial cells, and b) determining the viability of the bacterial cells after incubation.

The determined viability of the bacterial cells reflects/negatively correlates with the bioavailability of the metal ion in the composition such that a high viability indicates a low bioavailability, and a low viability indicates a high bioavailability.

The term "bioavailability" as used herein refers to the extent to which metal ions are available to reach a target area (preferably, the oral cavity) and provide an antimicrobial effect at the target area.

Preferably, the composition is aqueous. In some embodiments, the composition is an oral care composition. The term "oral care composition" as used herein means a product that in the course of ordinary usage is retained in the oral cavity for a time sufficient to contact some or all of the dental surfaces and/or oral tissues to achieve at least one oral health benefit. Oral health benefits include, without limitation, the prevention or treatment of mouth malodor, enamel erosion, dental caries, periodontal diseases and tooth hypersensitivity. The oral care composition may be provided in various forms including, without limitation, as a toothpaste, dentifrice, tooth gel, tooth powder, tablet, rinse, subgingival gel, foam, and mousse. When performing the method of the present invention, the oral care composition may be diluted or dissolved in an osmotically acceptable solvent (for example, phosphate-buffered saline) prior to incubating with bacterial cells.

Oral care compositions used or tested according to the methods defined herein may comprise one or more agents selected from surfactants, desensitizing agents, whitening agents, tartar control agents, binders, thickening agents, detergents, adhesion agents, foam modulators, pH modifying agents, mouth feel agents, sweeteners, flavorants, colorants, humectants, fluoride sources and combinations thereof.

In some embodiments, the composition is a skin care composition (for example, a liquid soap, a shower gel, or body cream). Skin care compositions may be applied to the skin and/or nails for therapeutic, prophylactic or cosmetic benefit. Skin care compositions may, for example, be used for enhancing the appearance, cleansing, controlling or improving odor, and improving the feel of skin and/or nails. Skin care compositions used or tested according to the methods defined herein may comprise one or more agents selected from dyes, fragrances, pH modifying agents, thickeners, viscosity modifiers, buffering agents, antioxidants, chelating agents, opacifiers, and humectants. When performing the method of the present invention, the skin care composition may be diluted or dissolved in an osmotically acceptable solvent (for example, phosphate-buffered saline) prior to incubating with bacterial cells.

In preferred embodiments, the composition comprising the metal ion further comprises a chelating agent. The chelating agent may be selected from tetrasodium pyrophosphate (TSPP), tetrapotassium pyrophosphate (TKPP), sodium tripolyphosphate (STPP), and ethylenediamine tetra-acetic acid (EDTA). The composition may consist essentially of water, the metal ion, and a chelating agent. The present inventors have found that the methods defined herein are useful for determining the effects of chelating agents on metal ion bioavailability, and that whilst chelating agents may increase the solubility of a metal ion, the bioavailability of a metal ion is not necessarily increased as a result.

In one arrangement, the compositions comprising the metal ion used or tested according to the methods defined herein are free from preservatives or any antimicrobial agents others than the metal ion. In this arrangement, any observed effect on the viability of the bacterial cells is solely attributable to the metal ions in the composition.

Typically in the methods defined herein, a mixture of bacterial cells is used. The bacterial cells may be selected from *Actinomyces viscosus, Lactobacillus casei, Streptococcus oralis, Fusobacterium nucleatum, Veillnoella parvula, Escherichia coli, Staphylococcus aureus* and *Serratia marcescens* or a mixture thereof.

In one arrangement, the bacterial cells comprise *Actinomyces viscosus, Lactobacillus casei, Streptococcus oralis, Fusobacterium nucleatum*, and *Veillnoella parvula*, preferably in a 1:1:1:1:1 ratio. This mixture simulates the complex flora of the oral environment. Thus, in one embodiment, the composition to be tested using a mixture of *Actinomyces viscosus, Lactobacillus casei, Streptococcus oralis, Fusobacterium nucleatum* and *Veillnoella parvula*, is an oral care composition as defined herein. The bacterial cells are typically cultured together in a continuous culture chemostat system prior to use in the methods described herein.

In another arrangement, the bacterial cells comprise *Escherichia coli, Staphylococcus aureus* and *Serratia marcescens*, preferably in a ratio of 0.45:0.45:0.1. This mixture is representative of normal skin flora. Thus, in one embodiment, the composition to be tested using a mixture of *Escherichia coli, Staphylococcus aureus* and *Serratia marcescens* is a skin care composition as defined herein. These bacterial cells are typically cultured separately in an overnight culture, prior to mixing in the ratio defined above and using in the methods described herein. Suitable methods and conditions of cell culturing would be known to a person skilled in the art of microbiology.

A sample of the bacterial culture is incubated with the test composition comprising the metal ions, preferably under conditions which would, in the absence of the test composition, be optimal for cell viability. In one arrangement, incubation is at 37° C. for 30 to 60 minutes. However, the incubation conditions may be adjusted according to the types of bacterial cells used. Typically, 1 ml of bacterial cell suspension comprising at least approximately $1 \times 10^6$ cells is incubated with the test composition.

After incubation with a test composition containing metal ions, the viability of the bacterial cells is determined. Methods and agents capable of distinguishing viable cells from non-viable cells would be known to a person skilled in the art of microbiology.

Typically, viability of bacterial cells is determined by means of a metabolic indicator dye. In one arrangement, after incubation with the test composition, the bacterial cells are washed and stained with the dye. Preferably, viability is determined using a redox-sensitive indicator dye. Redox-sensitive indicator dyes would be known to a person skilled in the art of microbiology and include tetrazolium-based dyes such as 3-(4,5-dimethylthiazol-2-yl)-2,5-diphenyltetrazolium bromide (MTT), 2,3-bis-(2-methoxy-4-nitro-5-sulfophenyl)-2H-tetrazolium-5-carboxanilide (XTT), 3-(4,5-dimethylthiazol-2-yl)-5-(3-carboxymethoxyphenyl)-2-(4-sulfophenyl)-2H-tetrazolium) (MTS), and 2-(2-methoxy-4-nitrophenyl)-3-(4-nitrophenyl)-5-(2,4-disulfophenyl)-2H-tetrazolium) (WST). NADH in metabolically active viable cells reduces tetrazolium compounds to brightly colored formazan products which may be detected by fluorescence spectroscopy at given excitation and emission wavelengths. Thus, the greater the fluorescence intensity, the greater the number of viable cells.

A particularly preferred metabolic indicator dye is resazurin (7-Hydroxy-3H-phenoxazin-3-one 10-oxide). In its oxidized state, resazurin is a blue, non-fluorescent dye. When viable bacterial cells are incubated with resazurin, the non-fluorescent dye is reduced to the pink dye resorufin. The fluorescence of the samples is read at 560 nm excitation and 590 nm emission to determine the proportion of viable bacterial cells.

Other indicators of viability include protease markers and ATP. For example, aminopeptidase activity present only in viable cells can be measured using a cell permeable fluorogenic substrate. Similarly, ATP may be measured using a beetle luciferase reaction, which uses ATP to generate light. Fluorescent staining systems (for example, the "backlight Live/Dead® system") which rely on membrane permeability as an indicator of bacterial viability are generally not suitable for the methods described herein, since metal ions, in general, do not permeabilize cell membranes.

Typically in the methods defined herein, the viability of the treated bacterial cells is quantified. In other words, the proportion of viable bacterial cells, as a percentage of the total number of bacterial cells incubated with the test composition containing the metal ions, may be determined. This may be done by determining the viability of standard mixtures of viable and non-viable bacterial cells (for example, standard mixtures of viable:non-viable cells corresponding to the bacterial mix used in the test assay in a ratio of 0:100, 20:80, 40:60, 60:40, 80:20 and 100:1), to generate a standard curve. Typically, the total number, type and concentration of bacterial cells in the standard mixes correspond to the total number, type and concentration of bacterial cells used in the assay. The viability results of the test composition may then be compared to those of the standard mixes to quantify the proportion of viable bacterial cells, as a percentage of the total number of bacterial cells.

The metal ion in the composition typically has antimicrobial, and in particular, antibacterial activity. Metal ions with antimicrobial activity would be known to a person skilled in the art of microbiology and include, without limitation, copper, cobalt, silver, manganese, nickel and zinc. Preferably, the metal ion is zinc. The composition may comprise one species or more than one species of metal ion. Metal ions in the composition are preferably provided in salt form. The salt may comprise a chloride, citrate or oxide. In a preferred embodiment, the salt comprises zinc chloride, zinc citrate or zinc oxide.

The present inventors have unexpectedly found that the solubility of a metal ion salt does not correlate with the bioavailability of the metal ion. The bioavailability of metal ions may be affected by numerous physical and biochemical parameters. These include stability in solution, stability at a given pH, and interference or competition by other compositional ingredients, in addition to the formation of insoluble or inactive complexes with other compositional ingredients. For example, a metal ion chelant such as EDTA may shift metal ions into the soluble fraction of a composition. However, when complexed with EDTA, the metal ions are not "available" to act on a desired physiological site to bring about a desired biological or clinical activity. The methods of determining bioavailability defined herein take into account the effects of such physical and biochemical parameters, and thus are advantage over methods comprising measuring solubility alone.

Uses

The methods defined herein may be used to determine the antimicrobial efficacy of a composition, optionally an oral care composition or a skin care composition, comprising a metal ion source. The composition and metal ion source may be as defined herein.

Additionally, the effect of an agent, preferably an oral care agent or a skin care agent, on the bioavailability of metal ions may be tested using the methods defined herein, by determining the bioavailability of metal ions in the presence and absence of the agent. Accordingly, provided is a use of the method as defined herein to evaluate the effect of an agent on the bioavailability of a metal ion in a composition comprising source of the metal ion and the agent. The composition and metal ion source may be as defined herein. The agent may be as defined below.

More specifically, there is provided a method of assessing the effect of an agent on the bioavailability of a metal ion in a composition comprising the metal ion, wherein the metal ion has antimicrobial activity, and the method comprises:
a) incubating a first sample of the composition comprising the metal ion with bacterial cells,
b) determining the viability of the bacterial cells after incubation,
c) incorporating the agent into a second sample of the composition comprising the metal ion,
d) incubating the second sample of the composition comprising the metal ion with bacterial cells,
e) determining the viability of the bacterial cells after incubation, and
f) comparing the viabilities determined in steps b) and e).

The composition, metal ion source, method of determining the viability of the bacterial cells in steps b) and e), and the bacterial cells themselves, may be as defined herein.

As discussed above, the determined viability of the bacterial cells reflects/negatively correlates with the bioavailability of the metal ion in the composition such that a high viability indicates a low bioavailability, and a low viability indicates a high bioavailability. A reduction in the metal ion bioavailability in the presence of the agent would indicate that the agent is not compatible with the metal ion, if antimicrobial activity is to be maintained.

In some embodiments, the agent is an oral care agent or a skin care agent. The term "oral care agent" refers to any agent suitable for incorporation into an oral care composition, and preferably, which has a therapeutic or prophylactic oral health benefit, or a cosmetic oral benefit. Similarly, the term "skin care agent" refers to any agent suitable for incorporation into a skin care composition, and preferably, which has a therapeutic, prophylactic or cosmetic skin care benefit.

In other embodiments, the agent is a chelating agent such as tetrasodium pyrophosphate (TSPP), tetrapotassium pyrophosphate (TKPP), sodium tripolyphosphate (STPP), and ethylenediamine tetra-acetic acid (EDTA).

The following Examples illustrate methods of the invention and their uses. The Examples are illustrative and do not limit the scope of the invention.

EXAMPLES

Example 1—Zinc Bioavailability (1)

The bioavailability of zinc in simple solutions of zinc salts (zinc chloride, zinc citrate and zinc oxide in sterilized, deionized water) with known differences in solubility, was determined. Test solutions were incubated with a mixture of *Actinomyces viscosus, Lactobacillus casei, Streptococcus oralis, Fusobacterium nucleatum*, and *Veillnoella parvula*, which had been grown together in a continuous culture system, for 1 hour at 37° C. (This bacterial mixture simulates the complex flora of the oral environment.) Subsequently, the cells were washed and mixed with 5 µg/ml resazurin solution. The fluorescence of the samples was read at 560 nm excitation and at 590 nm emission, and compared to standardized mixtures of viable and non-viable bacteria in order to determine the percentage of the total bacterial population that remained viable after treatment. The results are illustrated in Table 1. Each salt was tested at two different concentrations of zinc. The total amount of zinc was consistent between the different salts.

TABLE 1

Results of zinc salt assay

| Sample | % viable | Std. Error (%) |
| --- | --- | --- |
| PBS | 68.06 | 0.25 |
| 1/10 PBS | 68.73 | 0.18 |
| 1.7% $ZnCl_2$ | 2.58 | 1.80 |
| 0.17% $ZnCl_2$ | 31.48 | 0.96 |
| 2.6% ZnCitrate | 16.66 | 2.80 |
| 0.26% ZnCitrate | 44.90 | 2.71 |
| 1% ZnO | 14.70 | 2.90 |
| 0.1% ZnO | 48.57 | 1.99 |

As indicated in Table 1, all three zinc salts exhibited a dose-dependent response in terms of zinc bioavailability, when diluted ten-fold. However, it is known that zinc citrate is considerably more soluble than zinc oxide. However, in spite of this difference in solubility, the bioavailability of zinc was approximately the same with both salts, and at both zinc concentrations tested. These data demonstrate that solubility alone is not a good indicator of bioavailability. Without wishing to be bound by theory, it is possible that differences in bacterial adhesion or uptake of the metal ions by bacterial cells account for the observed differences in bioavailability.

Example 2—Effect of Citrate on Zinc Bioavailability

Previously it has been suggested that the addition of a citrate salt to zinc-containing compositions increases the amount of soluble zinc and therefore, the bioavailability of zinc (WO 2006012967A1, Unilever). To test this hypothesis, simple solutions of zinc salts in deionized water, in the presence and absence of varying levels of citrate, and at a pH typical of oral care compositions, were tested as described in Example 1. The results are illustrated in Table 2. The molar ratio of citrate to zinc is also indicated.

TABLE 2

Results of zinc salt and citrate assay

| Sample | % viable | Std. error (%) |
|---|---|---|
| ZnCitrate | 1.68 | 1.60 |
| ZnCitrate + KCitrate, pH 6.8; 2:1 | 32.57 | 2.88 |
| ZnCitrate + KCitrate, pH 8.1; 2:1 | 37.22 | 4.23 |
| ZnCitrate + KCitrate 1:1 | 8.97 | 1.15 |
| ZnCitrate + KCitrate 1:1.5 | 26.01 | 5.05 |
| ZnO | 23.75 | 4.89 |
| ZnO + KCitrate, pH 6.8; 2:1 | 38.35 | 3.79 |
| ZnO + KCitrate, pH 8.1; 2:1 | 39.05 | 3.99 |
| Dual Zn mix | 17.68 | 4.96 |
| Dual Zn + KCitrate, pH 6.8; 2:1 | 37.24 | 3.90 |
| Dual Zn + KCitrate, pH 8.1; 2:1 | 36.89 | 5.89 |

It can be seen from Table 2 that the addition of citrate to solutions of zinc oxide, zinc citrate or a mixture of both salts, whilst increasing the solubility of zinc, decreases the bioavailability of the metal ions, thus reducing the antimicrobial efficacy of the solutions. Thus it may be concluded that bioavailability of zinc is not simply a function of solubility.

Example 3—Effect of Chelators on Zinc Bioavailability

To determine the effects of chelators on the bioavailability of zinc, simple solutions of zinc citrate or zinc oxide, in deionized water in the presence or absence of chelators (tetrasodium pyrophosphate (TSPP), tetrapotassium pyrophosphate (TKPP), sodium tripolyphosphate (STPP) and ethylenediamine tetra-acetic acid (EDTA)) were tested in a bioavailability assay as described in Example 1. The amount of soluble zinc in each solution was also determined by centrifuging the solutions to remove insoluble zinc, and by testing the supernatant using ICP-AA (inductively coupled plasma with atomic absorption). The results are illustrated in Table 3 (zinc citrate solutions) and Table 4 (zinc oxide solutions).

TABLE 3 zinc citrate and chelator

| Sample | % Soluble zinc | % viable | Std. Error (%) |
|---|---|---|---|
| Zn Salt | 28.43 | 25.91 | 5.29 |
| Zn Salt + 10% TSPP | 91.25 | 54.40 | 9.76 |
| Zn Salt + 12.6% TKPP | 89.96 | 50.71 | 9.16 |
| Zn Salt + 14% STPP | 90.99 | 41.89 | 9.54 |
| Zn Salt + EDTA | 88.73 | 47.25 | 9.96 |

TABLE 4 zinc oxide and chelator

| Sample | % Soluble zinc | % viable | Std. Error (%) |
|---|---|---|---|
| Zn Salt | 0.00 | 32.26 | 4.18 |
| Zn Salt + 10% TSPP | 87.01 | 49.00 | 6.88 |
| Zn Salt + 12.6% TKPP | 99.49 | 48.40 | 7.74 |
| Zn Salt + 14% STPP | 50.00 | 27.95 | 7.12 |
| Zn Salt + EDTA | 95.28 | 44.89 | 9.28 |

Tables 3 and 4 illustrate that despite the solubility-enhancing effects of the chelators on the zinc salts, the zinc bioavailability did not increase in the presence of the chelators and in fact, often diminished in the presence of the chelators.

Example 4—Zinc Bioavailability (2)

The effect of simple solutions of zinc salts in deionized water (zinc citrate and zinc oxide) on the viability of a mixture of *Escherichia coli* (45%), *Staphylococcus aureus* (45%) and *Serratia marcescens* (10%) was tested. The incubation and detection methods used were as described in Example 1. The total amount of zinc was comparable between the test using zinc oxide and the test using zinc citrate. The results are illustrated in Table 5. Triclosan was used as a positive antimicrobial control for the experiment.

TABLE 5

Results of zinc salt assay

| Sample | % viable | Std. Error (%) |
|---|---|---|
| 0.4% ZnO | 67.23 | 5.49 |
| 0.8% Zn Citrate | 50.02 | 1.77 |
| 0.4% ZnO/0.2% Zn citrate | 56.16 | 4.26 |
| Triclosan | 18.83 | 3.20 |

As discussed above, zinc citrate is significantly more soluble than zinc oxide. However, Table 5 demonstrates that despite the significant difference in solubility, the bioavailability of zinc from zinc citrate was only marginally higher as compared to zinc oxide. Thus it may be concluded that solubility of a metal ion is not a good determinant of bioavailability.

Example 5—Copper Bioavailability

Bioavailability tests were conducted using simple copper solutions in deionized water. Solutions contained a final concentration of 0.5% or 0.05% elemental copper. The bioavailability test was performed as described in Example 1. The results are illustrated in Tables 6 and 7.

TABLE 6

0.5% Cu

| Sample | % viable | Std. Error (%) |
|---|---|---|
| $CuCl_2$ | 1.89 | 0.40 |
| CuO | 42.73 | 0.59 |
| $Cu_2O$ | 12.08 | 0.20 |
| $CuF_2$ | −6.91* | 0.40 |
| $CuSO_4$ | 5.82 | 0.60 |

*The viability in the presence of $CuF_2$ was below the detection level of the test

TABLE 7

0.05% Cu

| Sample | % viable | Std. Error (%) |
|---|---|---|
| $CuCl_2$ | 11.99 | 0.47 |
| CuO | 78.67 | 0.45 |
| $Cu_2O$ | 19.70 | 0.23 |

TABLE 7-continued 0.05% Cu

| Sample | % viable | Std. Error (%) |
|---|---|---|
| CuF$_2$ | 17.82 | 0.61 |
| CuSO$_4$ | 13.98 | 0.39 |

Tables 6 and 7 illustrate a dose-dependent response for all copper solutions tested (i.e. at the higher concentration, there was a reduced amount of viable bacteria indicating increased bioavailability of copper). The theoretical solubilities of the copper salts tested in water are as follows: CuCl$_2$: 75.7 g/100 ml; CuO: insoluble; Cu$_2$O: insoluble; CuSO$_4$: 20 g/100 ml. Thus, it can be seen that even though CuCl$_2$ has a significantly higher solubility than CuSO$_4$, the effects on bacterial cell viability (and thus the bioavailability of the copper ions) are comparable in both salts. Again, these data demonstrate that solubility of a metal ion alone is not a good determinant of its bioavailability.

Whilst particular embodiments of the invention have been illustrated and described, it will be obvious to those skilled in the art that various changes and modifications may be made without departing from the scope of the invention as defined in the appended claims.

What is claimed is:

1. A method for determining the effect of an oral care agent on the bioavailability of one or more zinc ions in a composition comprising a source of the zinc ions and bacterial cells, wherein the method comprises:
    a. incubating a sample of the composition comprising the source of the zinc ions and the bacterial cells with the oral care agent,
    b. determining the viability of the bacterial cells after the incubation by comparing the viability to the measurements obtained without the oral care agent,
    c. incorporating the oral care agent into a second sample of the composition comprising the source of the zinc ions and the bacterial cells,
    d. incubating the second sample of the composition comprising the source of the zinc ions and the bacterial cells with the oral care agent,
    e. determining the viability of the bacterial cells after the incubation, and
    f. comparing the viabilities as determined in steps b) and e);
        wherein the source of zinc ions comprises one or more zinc ion sources selected from the group consisting of: zinc chloride, zinc citrate, and zinc oxide;
wherein the oral care agent is selected from the group consisting of surfactants, desensitizing agents, whitening agents, tartar control agents, binders, thickening agents, detergents, adhesion agents, foam modulators, pH modifying agents, mouth feel agents, sweeteners, flavorants, colorants, humectants, fluoride sources, dyes, fragrances, viscosity modifiers, buffering agents, antioxidants, chelating agents, opacifiers and combinations thereof; and
wherein the bacterial cells are selected from the group consisting of: *Actinomyces viscosus, Lactobacillus casei, Streptococcus oralis, Fusobacterium nucleatum, Veillonella parvula, Escherichia coli, Serratia marcescens*, and a mixture thereof.

2. The method of claim 1, wherein the composition further comprises a chelating agent for chelating zinc.

3. The method of claim 2, wherein the chelating agent is selected from the group consisting of: tetrasodium pyrophosphate (TSPP), tetrapotassium pyrophosphate (TKPP), sodium tripolyphosphate (STPP), and ethylenediamine tetra-acetic acid (EDTA).

4. The method of claim 1, wherein the composition consists essentially of water, the source of zinc ions, and a chelating agent for the zinc ions.

5. The method of claim 1, wherein the composition is an oral care composition or a skin care composition.

6. The method of claim 1, wherein in step b), the viability of the bacterial cells is determined using a bacterial cell viability indicator dye.

7. The method of claim 6, wherein the bacterial cell viability indicator dye comprises a redox-sensitive indicator dye.

8. The method of claim 7, wherein the bacterial cell viability indicator dye comprises a tetrazolium-based dye.

9. The method of claim 8 wherein the bacterial cell viability indicator dye comprises a dye selected from the group consisting of: 3-(4,5-dimethylthiazol-2-yl)-2,5-diphenyltetrazolium bromide (MTT), 2,3-bis-(2-methoxy-4-nitro-5-sulfophenyl)-2H-tetrazolium-5-carboxanilide (XTT), 3-(4,5-dimethylthiazol-2-yl)-5-(3-carboxymethoxyphenyl)-2-(4-sulfophenyl)-2H-tetrazolium) (MTS), and 2-(2-methoxy-4-nitrophenyl)-3-(4-nitrophenyl)-5-(2,4-disulfophenyl)-2H-tetrazolium) (WST).

10. The method of claim 7, wherein the bacterial cell viability indicator dye comprises 7-hydroxy-3H-phenoxazin-3-one 10-oxide (resazurin).

11. The method of claim 1, wherein the bacterial cells comprise *Actinomyces viscosus, Lactobacillus casei, Streptococcus oralis, Fusobacterium nucleatum*, and *Veillonella parvula*.

12. The method of claim 1, wherein the bacterial cells comprise *Escherichia coli, and Serratia marcescens*.

13. The method of claim 1, wherein the source of the zinc ions is a salt of the zinc ions.

14. The method of claim 1, wherein the oral care agent is a zinc ion chelating agent.

15. The method of claim 14, wherein the chelating agent is selected from the group consisting of tetrasodium pyrophosphate (TSPP), tetrapotassium pyrophosphate (TKPP), sodium tripolyphosphate (STPP), and ethylenediamine tetra-acetic acid (EDTA).

16. The method of claim 1, wherein the composition consists essentially of water and the zinc ions.

17. The method of claim 1, wherein in step b) and in step e), the viability of the bacterial cells is determined using a bacterial cell viability indicator dye.

18. The method of claim 17, wherein the bacterial cell viability indicator dye comprises a redox-sensitive indicator dye.

19. The method of claim 18, wherein the bacterial cell viability indicator dye comprises a tetrazolium-based dye.

20. The method of claim 19, wherein the bacterial cell viability indicator dye comprises a dye selected from one of the group consisting of: 3-(4,5-dimethylthiazol-2-yl)-2,5-diphenyltetrazolium bromide (MTT), 2,3-bis-(2-methoxy-4-nitro-5-sulfophenyl)-2H-tetrazolium-5-carboxanilide (XTT), 3-(4,5-dimethylthiazol-2-yl)-5-(3-carboxymethoxyphenyl)-2-(4-sulfophenyl)-2H-tetrazolium) (MTS), and 2-(2-methoxy-4-nitrophenyl)-3-(4-nitrophenyl)-5-(2,4-disulfophenyl)-2H-tetrazolium) (WST).

21. The method of claim 18, wherein the bacterial cell viability indicator dye comprises 7-hydroxy-3H-phenoxazin-3-one 10-oxide (resazurin).

* * * * *